(12) United States Patent
Belafsky

(10) Patent No.: US 8,777,840 B2
(45) Date of Patent: *Jul. 15, 2014

(54) ENDOSCOPIC TUBE DELIVERY SYSTEM

(75) Inventor: Peter C. Belafsky, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/947,750

(22) Filed: Nov. 16, 2010

(65) Prior Publication Data

US 2011/0257476 A1 Oct. 20, 2011

Related U.S. Application Data

(63) Continuation of application No. 11/795,398, filed as application No. PCT/US2006/001877 on Jan. 18, 2006, now Pat. No. 7,857,750.

(60) Provisional application No. 60/644,905, filed on Jan. 18, 2005.

(51) Int. Cl.
  *A61B 1/00* (2006.01)

(52) U.S. Cl.
  USPC ............ 600/104; 600/114; 600/121; 600/123; 600/128; 600/153

(58) Field of Classification Search
  USPC ................. 600/104–107, 121, 123, 127, 129
  See application file for complete search history.

(56) References Cited

U.S. PATENT DOCUMENTS

| | | | |
|---|---|---|---|
| 4,182,342 A | 1/1980 | Smith | |
| 4,249,535 A | 2/1981 | Hargest, III | |
| 4,384,584 A | 5/1983 | Chen | |
| 4,410,320 A | 10/1983 | Dykstra et al. | |
| 4,634,425 A | 1/1987 | Meer | |
| 4,672,960 A * | 6/1987 | Frankel | 128/200.26 |
| 4,704,111 A | 11/1987 | Moss | |
| 4,778,448 A | 10/1988 | Meer | |
| 4,790,832 A | 12/1988 | Lopez | |
| 4,828,550 A | 5/1989 | Kurimoto | |
| 4,874,365 A | 10/1989 | Frederick et al. | |
| 4,895,562 A | 1/1990 | Lopez | |
| 5,085,216 A | 2/1992 | Henley, Jr. et al. | |
| 5,167,220 A | 12/1992 | Brown | |

(Continued)

FOREIGN PATENT DOCUMENTS

JP 2006-87687 A 6/2004
JP 2006-314802 A 11/2006

OTHER PUBLICATIONS

Mitchell, et al., "Transnasal Endoscopic Technique for Feeding Tube Placement," 1992, Gastrointestinal Endoscopy, vol. 38, No. 5, 596-597.

(Continued)

*Primary Examiner* — Matthew J Kasztejna
(74) *Attorney, Agent, or Firm* — Kilpatrick Townsend & Stockton LLP

(57) ABSTRACT

An apparatus is disclosed. In some embodiments, the apparatus comprises an endoscope comprising a first distal end portion, and a tube comprising a second distal end portion, wherein the endoscope and the tube are in a side-by-side relationship and are coupled at distal end portions of the endoscope and the tube using a single coupling device.

6 Claims, 5 Drawing Sheets

(56) References Cited

U.S. PATENT DOCUMENTS

| | | | |
|---|---|---|---|
| 5,322,513 | A | 6/1994 | Walker |
| 5,334,167 | A * | 8/1994 | Cocanower ................ 604/523 |
| 5,554,140 | A | 9/1996 | Michels et al. |
| 5,665,052 | A | 9/1997 | Bullard |
| 5,846,181 | A | 12/1998 | Heckele et al. |
| 6,322,495 | B1 | 11/2001 | Snow et al. |
| 6,506,150 | B1 | 1/2003 | Ouchi |
| 6,712,757 | B2 | 3/2004 | Becker et al. |
| 6,878,106 | B1 * | 4/2005 | Herrmann ................ 600/104 |
| 6,997,931 | B2 | 2/2006 | Sauer et al. |
| 7,081,097 | B2 * | 7/2006 | Martone et al. ............ 600/562 |
| 7,566,300 | B2 * | 7/2009 | Devierre et al. ............ 600/104 |
| 7,670,282 | B2 * | 3/2010 | Mathis ........................ 600/104 |
| 2001/0000040 | A1 * | 3/2001 | Adams et al. ................ 600/121 |
| 2002/0107530 | A1 * | 8/2002 | Sauer et al. ................ 606/139 |
| 2002/0183591 | A1 * | 12/2002 | Matsuura et al. ............ 600/127 |
| 2003/0195387 | A1 * | 10/2003 | Kortenbach et al. ........ 600/104 |
| 2004/0064017 | A1 * | 4/2004 | Cappiello et al. ............ 600/156 |
| 2004/0230095 | A1 | 11/2004 | Stefanchik et al. |
| 2004/0230096 | A1 | 11/2004 | Stefanchik et al. |
| 2004/0230097 | A1 | 11/2004 | Stefanchik et al. |
| 2006/0069304 | A1 | 3/2006 | Takemoto |
| 2006/0258907 | A1 | 11/2006 | Stefanchik |
| 2006/0259010 | A1 * | 11/2006 | Stefanchik et al. .......... 604/525 |
| 2006/0281970 | A1 | 12/2006 | Stokes et al. |
| 2007/0203393 | A1 | 8/2007 | Stefanchik |
| 2008/0103357 | A1 | 5/2008 | Zeiner |

OTHER PUBLICATIONS

Pleatman et al., "Endoscopic Placement of Feeding Tubes in the Critically Ill Patient," Jul. 1987, Surgery, Gynecology & Obstetrics, vol. 165, 69-70.

Stark et al., "Endoscopically Place Nasoenteral Feeding Tubes: Indications and Techniques." Apr. 1991, The American Surgeon, vol. 57, No. 4, 203-205.

International Search Report from PCT/US09/35460, mailed Jul. 17, 2009 (3 pages).

Written Opinion of the International Searching Authority from PCT/US09/35460, mailed Jul. 17, 2009 (9 pages).

Office Action of Dec. 30, 2009 in related U.S. Appl. No. 11/795,398.

International Search Report from PCT/US06/01877, mailed Sep. 24, 2007 (3 pages) in related U.S. Appl. No. 11/795,398.

Written Opinion of the International Searching Authority from PCT/US06/01877, mailed Sep. 24, 2007 (7 pages) in related U.S. Appl. No. 11/795,398.

Notice of Allowance of Aug. 19, 2010 in related U.S. Appl. No. 11/795,398.

Japanese Office Action mailed Jun. 14, 2013 in JP Application No. 2010-548900, with translation.

* cited by examiner

US 8,777,840 B2

ENDOSCOPIC TUBE DELIVERY SYSTEM

CROSS-REFERENCE TO RELATED APPLICATIONS

This application is a continuation of U.S. patent application Ser. No. 11/795,398, filed on Jul. 18, 2007, which is the National Stage entry of International Application No. PCT/US2006/001877, filed on Jan. 18, 2006, which claims the benefit of U.S. Provisional Application No. 60/644,905, filed on Jan. 18, 2005, all of which are herein incorporated by reference in its entirety for all purposes.

BACKGROUND OF THE INVENTION

Clinicians who want to place a nasal-jejunal feeding tube in their patients currently rely on gravity and peristalsis to carry a blindly passed feeding tube from the stomach into the jejunum, fluoroscopy to pass the feeding tube under radiologic guidance, or per-oral sedated endoscopy to guide a blindly passed transnasal tube from the stomach into the jejunum.

Each of the above-noted procedures is undesirable for one reason or another. For example, the blind placement of a feeding tube into a patient can result in the inadvertent intubation of the trachea and possible bronchopleural injuries. Fluoroscopic placement methods are complicated and require the assistance of a radiology department. Sedation is not desirable and poses an inherent risk.

Another approach is described in Damore et al., "Prospective evaluation of a new through-the-scope nasoduodenal enteral feeding tube", Surgical Endoscopy, 1997 May; 11(5); 460. This paper describes the use of a bulky per-oral endoscope that requires intravenous sedation. An endoscope is fed through the mouth of a patient and the distal end of the endoscope is placed in the small intestine. A feeding tube that is about twice the length of the endoscope is passed through the endoscope. The feeding tube is then kept in the small intestine and the endoscope is removed over it. This "through the scope" tube placement uses a large caliber per oral esophagoscope. Once the tube is inserted through the mouth and into the intestine, the feeding tube must be transferred from the mouth to the nose. This nasal transfer can be time consuming, difficult, and uncomfortable. In addition, this procedure requires intravenous sedation that poses inherent cost and risk to the patient.

This method also has a number of disadvantages. For example, the procedure is somewhat complex and uses sedation. It would be desirable to provide for a method that is less complex and does not use sedation. Additionally, the endoscope that is used has a large diameter as it needs to accommodate a feeding tube. The endoscope is too large to fit through a nasal cavity of a patient. This is why the complex insertion procedure that is described above is used.

Another method uses a dangling suture at an end of a feeding tube. Forceps in an endoscope are used to "pull" the tube along. This method is also undesirable, as it is difficult to have the forceps grab the single suture. It is also a complicated way to join an endoscope and a feeding tube using multiple mechanisms.

Thus, an improved apparatus and method for inserting a tube such as a feeding tube into a patient is desired. Embodiments of the invention address these and other problems.

BRIEF SUMMARY OF THE INVENTION

Embodiments of the invention are directed to apparatuses and methods that can be used to insert a tube, such as a feeding tube, into a patient. The apparatuses and methods are desirably used without sedation and without fluoroscopy.

One embodiment of the invention is directed to an apparatus comprising an endoscope comprising a first distal end portion, and a tube comprising a second distal end portion. The first distal end portion of the endoscope and the second distal end portion of the tube are in a side-by-side relationship. They are also detachably coupled together at the distal end portions using a single coupling device.

Another embodiment of the invention is directed to a method for using the above noted apparatus. The method includes inserting the first distal end portion of the endoscope and the second distal end portion of the tube into a cavity of a patient. The cavity may be the patient's nasal cavity. After the first and second distal end portions are inserted into the patient, the first and second distal end portions are uncoupled from each other. The endoscope is then no longer mechanically coupled to the feeding tube and the endoscope is withdrawn from the patient.

Another embodiment of the invention is directed to a method for making an apparatus, the method comprising obtaining an endoscope comprising a first distal end portion, and obtaining a tube comprising a second distal end portion. The first distal end portion of the endoscope is then attached to the second distal end portion of the tube so that at least the first distal end portion of the endoscope and the second distal end portion of the tube are detachably coupled together in a side-by-side relationship using a single coupling device. The first distal end portion of the endoscope and the second distal end portion of the tube are capable of being uncoupled when they are present in a patient.

Another embodiment of the invention is directed to an apparatus comprising: an endoscope comprising a first distal end portion; a tube comprising a second distal end portion, wherein the endoscope and the tube are in a side-by-side relationship and are detachably coupled at the first distal end portion of the endoscope and the second distal end portion of the tube using a coupling device comprising a loop of material; and a guidewire in the tube, the guidewire being coupled to the coupling device.

These and other embodiments of the invention are described in further detail below.

DETAILED DESCRIPTION

Figure 1:
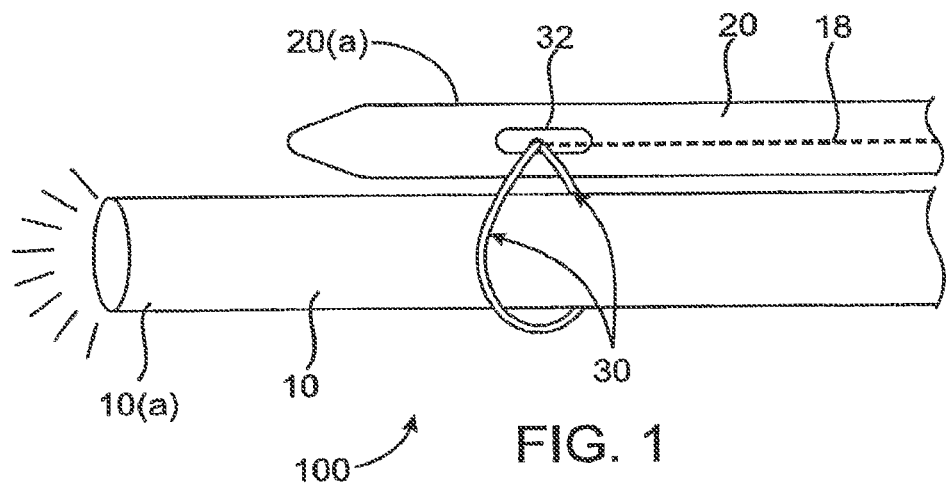
FIG. 1 shows a schematic view of an apparatus including a coupling device coming out of a distal feeding port of a feeding tube to secure the feeding tube to the endoscope.

Technology has recently become available that allows a clinician to examine the upper gastrointestinal tract of a patient with a thin endoscope (5.1 mm in diameter) passed through the nasal cavity in an unsedated patient (e.g., a Pentax VE-1530 transnasal esophagoscope). Embodiments of the invention allow one to directly deliver transnasal feeding tubes into the jejunum using such ultra-thin transnasal endoscopes. Embodiments of the invention eliminate the need for radiography, sedated per-oral esophagoscopy, pH monitoring, and/or intravenous sedation when placing a feeding tube into the stomach or jejunum (or other internal body structure) of a patient.

In a preferred embodiment, the apparatus comprises a flexible feeding tube with a band or suture affixed to the distal end portion of the tube. The band would emerge from a distal port on the tube and attach onto an ultra-thin endoscope thus securing the tube to the scope. The feeding tube would have a typical guidewire through its center lumen. After the endoscopy has been performed and the distal end portion of the feeding tube is located in the small bowel, removal of the guidewire will release the band or suture, thus separating the tube from the endoscope. The endoscope can then be removed and the feeding tube will stay in place at its final destination. Since the distal end portion of the feeding tube is placed directly in the bowel, no radiograph will be necessary to confirm placement.

Additionally, other devices can also secure an ultrathin endoscope (e.g., a Pentax VE-1530 transnasal esophagoscope) to a traditional nasal jejunal feeding tube. In some embodiments, specialized forceps would fit through a 2 mm biopsy channel of the esophagoscope. A loop or band would be affixed to the distal end portion of long forceps. The loop would grasp the feeding tube and secure the tube to the endoscope. Once the feeding tube and endoscope enter the jejunum, the forceps would be relaxed and the band would release the tube into the jejunum. The endoscope could then be safely withdrawn from the patient leaving the tube at its final destination.

An apparatus according to an embodiment of the invention comprises an endoscope having a first distal end portion, and a tube having a second distal end portion. The tube is preferably a feeding tube such as a nasojejunal feeding tube. Although feeding tubes are discussed in detail, other tubes such as air tubes can be used in other embodiments.

The endoscope and the tube are in a side-by-side relationship and are detachably coupled at first and second distal end portions of the endoscope and the tube, respectively. A coupling device may detachably couple the distal end portions of the endoscope and the tube.

Any suitable coupling device may be used in embodiments of the invention. A single coupling device according to embodiments of the invention may take any form as long as it is able to detachably couple at least the distal end portions of an endoscope and a feeding tube (or other type of tube). As used herein, "detachably couple" refers to the ability of the coupling device to temporarily couple at least the distal end portions of an endoscope and feeding tube. The single coupling device may be integral with or separable from the endoscope or feeding tube. The single coupling device may include a single loop, band, clip, harness, adhesive, etc., which may be attached to, integral with, or separate from the distal end portions of the endoscope and/or the feeding tube.

The coupling device may be capable of being in a coupled state where the distal end portions of the endoscope and the feeding tube are coupled together, or an uncoupled state where the distal end portions of the endoscope and the feeding tube are not coupled together. The coupling device is in a coupled state when the distal end portions of the endoscope and the feeding tube are being inserted into a patient. After the distal end portions of the endoscope and the feeding tube arrive at their destination within the patient, the coupling device may be transformed into an uncoupled state.

The transformation to the uncoupled state may take place with or without the active manipulation of the coupling device by a party such as a medical assistant or physician. For example, in some embodiments, the coupling device may take the form of a biocompatible degradable adhesive that temporarily joins the distal end portions of the endoscope and the feeding tube as they are being inserted into a patient. After a predetermined amount of time, the adhesive may degrade thus uncoupling the previously coupled distal end portions. In another example, the coupling device may include sheath or loop of material that surrounds both the distal end portions of the feeding tube and the endoscope. It may alternatively surround the endoscope distal end portion and may be attached to the distal end portion of the feeding tube. After the distal end portions are inserted into a patient, the endoscope may be withdrawn from the sheath or loop of material.

In other embodiments, the transformation to the uncoupled state may take place with the active direct, or indirect, manipulation of the coupling device by a person such as a medical assistant or physician. As will be explained in detail below, in some embodiments, a guidewire that is inside of the feeding tube may be manipulated by a person and this manipulation may in turn manipulate the coupling device so that it transforms into an uncoupled state. For instance, the guidewire may be pulled, twisted, or otherwise actuated so that this force is transmitted to the coupling device. If the coupling device contains a material that has a tensile strength that is less than the pulling or twisting force applied to the guidewire, the coupling device may thereafter break, thereby uncoupling the distal end portions of the endoscope and the feeding tube. In another embodiment, the actuation of the guidewire may actuate a coupling device that may include a clamp, forceps, or the like at the distal ends of the endoscope and the feeding tube. The actuation of the clamp, forceps, or the like may release the endoscope from the feeding tube (or vice-versa), thereafter allowing the endoscope to be withdrawn from the patient.

Specific examples described in further detail below with reference to the Figures.

FIG. 1 shows a schematic view of an apparatus 100 according to an embodiment of the invention. The apparatus 100 includes an endoscope 10 including a first distal end portion 10(a), and a feeding tube 20 with a second distal end portion 20(a). For clarity of illustration, the endoscope 10 and the feeding tube 20 are not shown in their entirety. The first distal end portion 10(a) of the endoscope 10, and the second distal end portion 20(a) of the feeding tube 20 are detachably coupled together with a coupling device 30. The feeding tube 20 may comprise a biocompatible, flexible, polymeric material such as PVC.

In this example, the coupling device 30 may be in the form of a loop of material, and the loop of material may emanate from a region 32 of the feeding tube 20. In this example, the region 32 may be in the form of an aperture (i.e., a feeding port) that is a passage for fluids or food to pass from inside of the feeding tube 20 to the outside of the feeding tube 20, and to a patient.

A guidewire 18 may be present in the feeding tube 20 and may be used to stiffen the feeding tube 20 as it is being fed into a patient. The guidewire 18 may be attached to the coupling device 30. In some embodiments, when the guidewire (or other axially-oriented, elongated device) is manipulated, the coupling device 30 is also manipulated. The manipulation of the coupling device 30 causes the coupling device 30 to change from a coupled state to an uncoupled state. For example, if the coupling device 30 is in the form of a loop of material, the loop of material may be made of a material that has a lower tensile strength than the guidewire 18. Hone pulls on the guidewire 18, the loop of material may break thereby changing the coupling device 30 to an uncoupled state. Once the first distal end portion 10(a) of the endoscope 10 and the second distal end portion 20(a) of the feeding tube 20 are uncoupled from each other, the endoscope 20 may be withdrawn from the patient.

The feeding tube 20 and the endoscope 10 may have any suitable dimensions. In preferred embodiments, they may have dimensions so that they are insertable into a nasal cavity of an ordinary patient. For example, the outer diameter of at least the distal end portion of the endoscope 10 may be about 5.1 mm or less. The outer diameter of at least the distal end portion of the feeding tube 20 may be about 6 mm (preferably 5 mm) or less. The lengths of the feeding tube 20 and the endoscope 10 may be between about 60 to 120 centimeters, and they may be of generally equal length in sonic instances.

Figure 2:
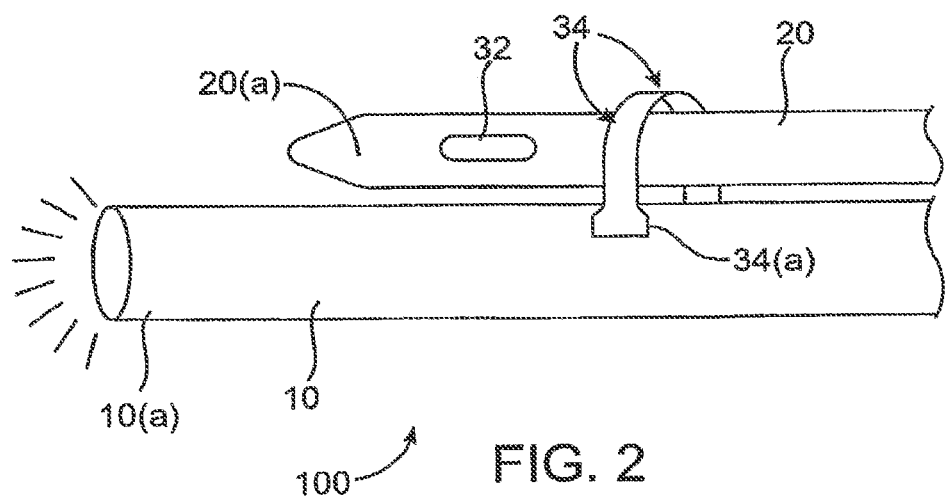
FIG. 2 shows a schematic view of an apparatus including a coupling device securing an endoscope to a feeding tube. The coupling device is attached to an external portion of the endoscope and loops around the feeding tube.

FIG. 2 shows a schematic view of another apparatus 100 according to another embodiment of the invention. In FIG. 2, like numerals designate like elements as in FIG. 1. However, in FIG. 2, the coupling device 34 is different than the coupling device 30 in FIG. 2. In this example, the coupling device 34 is in the form of an arc of material, where the ends of the arc of material are coupled to the distal end portion 10(a) of the endoscope 10 at two attachment regions 34(a). Unlike the embodiment in FIG. 1, the feeding tube 20 passes through the arc of material forming the coupling device 34, instead of the endoscope 20 passing through a loop of material.

Figure 3:
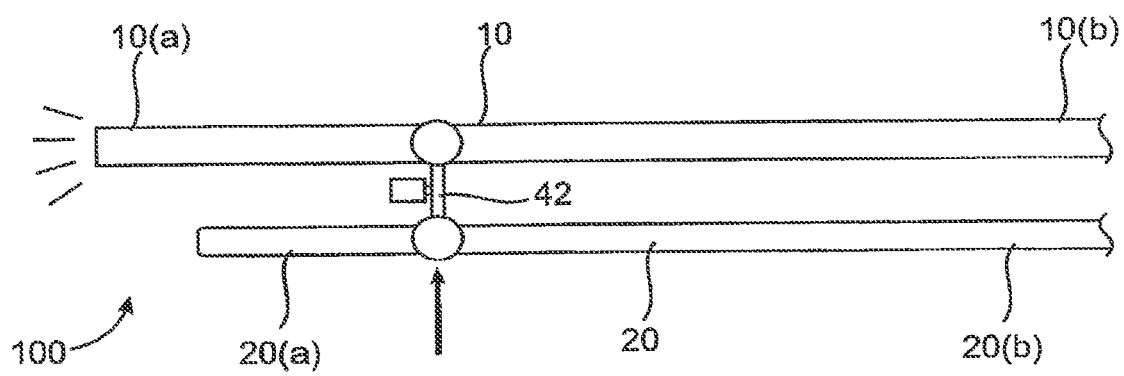
FIG. 3 shows a schematic view of an apparatus including a coupling device that secures external portions of a feeding tube and an endoscope.

FIG. 3 shows a schematic view of another apparatus 100 according to an embodiment of the invention. In FIG. 3, like numerals designate like elements as in FIGS. 1 and 2. However, in FIG. 3, the coupling device 42 is different than the previously described coupling devices. The coupling device 42 in this example is a device that is physically separate from the endoscope 10 and the feeding tube 20 and external to them, but is otherwise attached to them. In one example, the coupling device 42 may be a clip or the like that contains a material that has a tensile strength that is lower than the pulling force that is applied to the endoscope 10. The pulling force may break a portion of the coupling device 42 thereafter allowing the endoscope 10 and the feeding tube 20 to be separated from each other.

Figure 4:
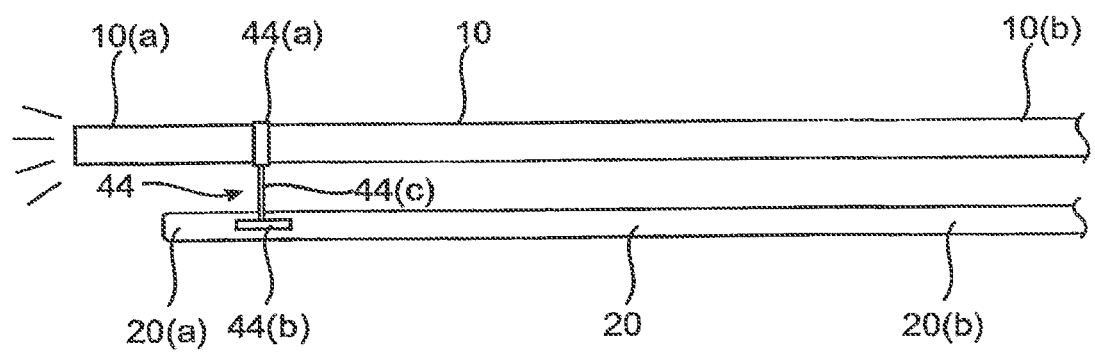
FIG. 4 shows a schematic view of an apparatus including a coupling device that is located partially inside of the feeding tube and connects to an external portion of the endoscope.

FIG. 4 shows a schematic view of an apparatus 100 according to an embodiment of the invention. In FIG. 4, like numerals designated like elements as in FIGS. 1-3. In FIG. 4, the coupling device 44 is a device that is separate from the endoscope 10 and the feeding tube 20, and is engaged with their distal end portions 10(a), 10(b). In this example, one end 44(b) of the coupling device 44 is located partially inside of the feeding tube 20, and is co-linear with the feeding tube 20, while the other end 44(a) connects to an external portion of the endoscope 10. A bridge 44(c) may connect the two ends 44(a), 44(b) of the coupling device 44. This bridge 44(c) may comprise a material that has a tensile strength lower than the force needed to pull the endoscope 10 out of a patient. A portion of the bridge 44(c) may pass through a feeding port in the feeding tube 20.

The apparatuses according to embodiments of the invention may be formed in any suitable manner. For example, an endoscope comprising a first distal end portion may be obtained. As noted above, a preferred endoscope has a maximum outer dimension of about 5.1 mm and such endoscopes are commercially available. Then, a tube comprising a second distal end portion is obtained. This tube may be manufactured, purchased, or otherwise obtained. Then, the first distal end portion of the endoscope is attached to the second distal end portion of the tube so that the at least the first distal end portion of the endoscope and the second distal end portion of the tube are in a side-by-side relationship. As noted above, the coupling device that is used to attach the distal end portions can be preformed with either or both of the endoscope or the feeding tube, or may be separate from them and attached to both of them to couple them together.

Figure 5:
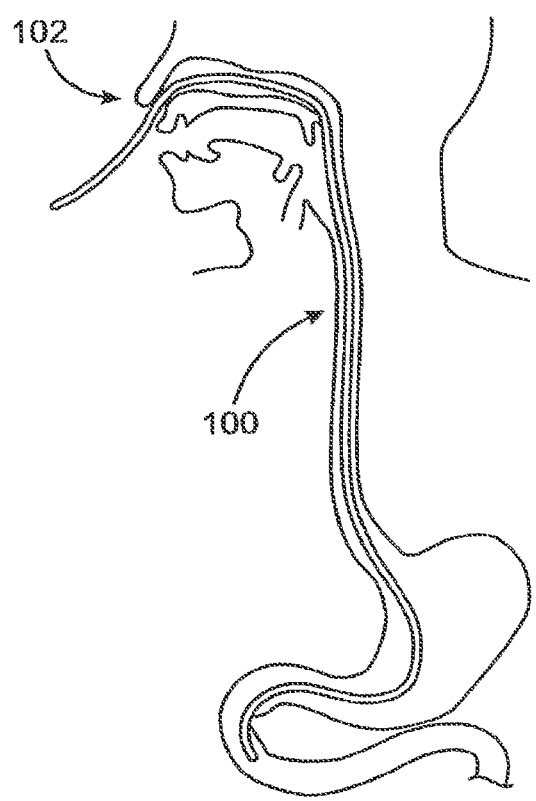
FIG. 5 shows a schematic view of an apparatus according to an embodiment of the invention as it would be present in a patient.

FIG. 5 shows a schematic view of an apparatus 100 as it would be present in a patient. As shown in FIG. 5, the apparatus 100 may have any of the above-noted configurations. At least a portion of an apparatus 100 is inserted into the patient, and the coupled distal ends of the endoscope and the feeding tube are guided through a nasal cavity 102 of the patient, through the esophagus, to the stomach and into the small intestine, where the distal ends arrive at their destination. Once they are at their destination, they are uncoupled from each other as described above. After the distal end portions are uncoupled, the endoscope is withdrawn from the patient and the feeding tube remains in the patient.

It is apparent that the methods for inserting transnasal feeding tubes according to embodiments of the invention are less complicated and safer for a patient than conventional procedures. For example, instead of placing a feeding tube into a patient's mouth and then manipulating it so that its proximal end passes through the nasal cavity of a patient, the apparatus according to embodiments of the invention can be inserted into the nasal cavity of a patent and guided to its destination within a patient. The endoscope can thereafter be easily and safely withdrawn from the patient in embodiments of the invention.

Figure 6A:
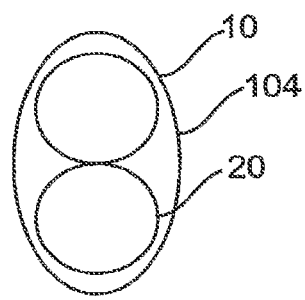
FIGS. 6(a) and 6(b) respectively show schematic illustrations of how an embodiment of the invention can fit within a nasal cavity of a patient, while a conventional tube-in-a-tube endoscope/feeding tube arrangement can't fit within a nasal cavity of a patient.
Figure 6B:
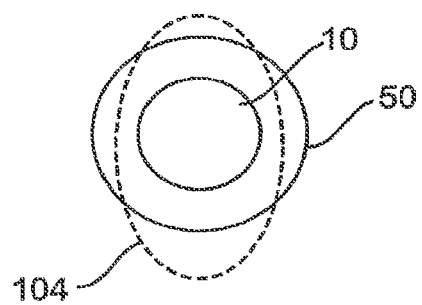

FIGS. 6(a) and 6(b) respectively show schematic illustrations of how an embodiment of the invention can fit within a nasal cavity of a patient, while a conventional tube-in-a-tube endoscope arrangement cannot fit with a nasal cavity of a patient.

FIG. 6(a) shows a side-by-side endoscope 10 and feeding tube 20 pair fitting within an oblong configuration 104 representing a nasal cavity. In comparison, FIG. 6(b) shows a conventional tube-in-a-tube configuration including a larger endoscope 50 and a feeding tube 10. As shown in FIG. 6(b), the illustrated configuration cannot fit through the oblong configuration 104 representing an ordinary nasal cavity. It therefore must be introduced through the mouth of a patient, instead of the patient's nasal cavity as described in the Background section above.

Figure 7:
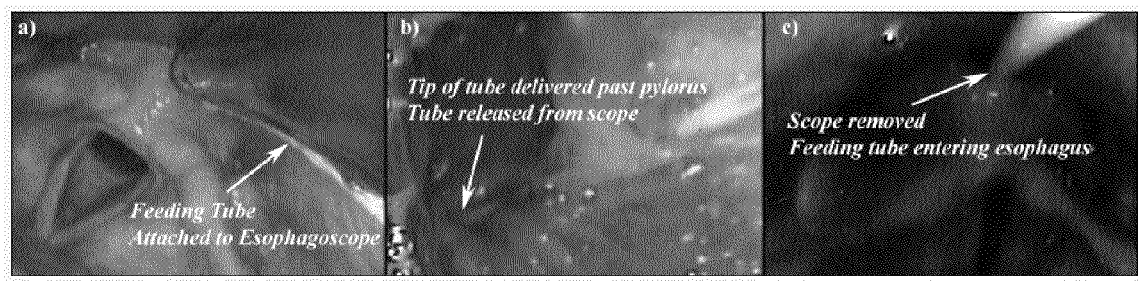
FIG. 7(a) shows a feeding tube as it is attached to an esophagoscope.
FIG. 7(b) shows a tube as it is delivered past the pylorus, and as the tube is released from the scope.
FIG. 7(c) shows the scope as it is being removed and after the feeding tube has entered the esophagus.

FIGS. 7(a)-7(b) are images that show the use of embodiments of the invention. FIG. 7(a) shows a feeding tube attached to small caliber endoscope. The attached tube and endoscope are entering the esophagus together. Both are going through the nose. FIG. 7(b) shows the tip of the feeding tube past the pylorus after the tube has been released from the endoscope. FIG. 7(c) shows a feeding tube entering the esophagus after the endoscope has been withdrawn. This procedure was performed on an unsedated patient in less than 5 minutes. Although these images do not show the device attaching the endoscope to the feeding tube, they demonstrate that the procedure is technically straightforward, feasible, safe, and takes very little time to perform.

There are many advantages that are provided by embodiments of the invention.

First, embodiments of the invention are safer for the patient. In embodiments of the invention, a tube and endoscope are placed together through the nose without the need for intravenous sedation. Most complications of endoscopy are caused by the sedation, not the procedure. This apparatuses and methods according to embodiments of the invention do not require any radiation exposure as compared to other techniques of tube placement. Embodiments of the invention can also be performed at the bedside in a timely fashion. Transferring a critically ill patient out of the ICU (intensive care unit) to the place where fluoroscopy is performed can be problematic. The endoscopic placement of feeding tubes eliminates the risk of inadvertently placing a feeding tube into a patient's lung. Such erroneous feeding tube placement is relatively common with the blind placement of feeding tubes, and food administered through a feeding tube into the lung can have grave consequences.

Second, embodiments of the invention are less expensive for hospitals and the medical community. Because embodiments of the invention do not require sedation, patient transfer, or radiography, they can be performed at a much lower cost.

Third, embodiments of the invention provide critical care specialists with a new procedure. The procedures performed using embodiments of the invention reimburse well and are not technically difficult. Clinicians are more likely to use embodiments of the invention and order/perform them if they are easy to perform and if the clinicians will be reimbursed for their services.

Fourth, the coupling device that is used in embodiments of the invention is simple and reliable and does not require the use of complicated joining mechanisms.

In summary, embodiments of the invention are safer for the patient, better for the clinician, and less expensive than conventional tube placement apparatuses and methods.

All patent applications, patents, and publications mentioned above are herein incorporated by reference in their entirety for all purposes.

Any recitation of "a", "an" or "the" is intended to mean "one or more" unless specifically indicated to the contrary.

The above description is illustrative but not restrictive. Many variations of the invention will become apparent to those skilled in the art upon review of the disclosure. The scope of the invention should, therefore, be determined not with reference to the above description, but instead should be determined with reference to the pending claims along with their full scope or equivalents. Moreover, the features of one or more embodiments of the invention may be combined with one or more features of other embodiments of the invention without departing from the scope of the invention.

What is claimed is:

1. A coupling device for coupling a commercially available endoscope to a feeding tube, the coupling device comprising:
    a bridge having a first end portion and a second end portion;
        wherein the first end portion is configured to externally and removeably couple to a distal portion of the commercially available endoscope;
        wherein the second end portion is configured to couple internally within the feeding tube such that the coupling device is partially inside a distal portion of the feeding tube;
    wherein the bridge positions the endoscope and the feeding tube in a side-by-side relationship when the first end portion is externally coupled to the distal portion of the commercially available endoscope and the second end portion is coupled internally within the feeding tube,
    wherein the apparatus further comprises a guide wire inside of the feeding tube, wherein the guide wire is coupled to the bridge and is adapted to manipulate the bridge to uncouple the endoscope and feeding tube.

2. The apparatus of claim 1 wherein in the side-by-side relationship the coupled endoscope and the tube are configured to fit within a nasal cavity of an adult patient.

3. The apparatus of claim 1 wherein the endoscope and the tube are approximately the same length.

4. The apparatus of claim 1 wherein the coupling device comprises a material that can break to uncouple the first distal end portion and the second distal end portion.

5. The apparatus of claim 1 wherein the feeding tube is a nasojejunal feeding tube.

6. A method for making an apparatus, the method comprising:
    obtaining commercially available endoscope comprising a first distal end portion;
    obtaining a feeding tube comprising a second distal end portion; and
    attaching the first distal end portion of the commercially available endoscope to the second distal end portion of the feeding tube so that at least the first distal end portion of the endoscope and the second distal end portion of the tube are detachably coupled using a coupling device and are in a side-by-side relationship,
    wherein the coupling device comprises:
    a bridge having a first end portion and a second end portion;
        wherein the first end portion is configured to externally and removeably couple to the first distal end portion of the commercially available endoscope;
        wherein the second end portion is configured to couple internally within the feeding tube such that the coupling device is partially inside the second distal end portion of the feeding tube;
        wherein the bridge positions the endoscope and the feeding tube in the side-by-side relationship when the first end portion is externally coupled to the distal portion of the commercially available endoscope and the second end portion is coupled internally within the feeding tube;
    wherein the first distal end portion of the commercially available endoscope and the second distal end portion of the feeding tube are capable of being uncoupled when they are present in a patient
    wherein a guide wire is included inside of the feeding tube, wherein the guide wire is coupled to the bridge and is adapted to manipulate the bridge to uncouple the endoscope and feeding tube.

* * * * *